United States Patent [19]

Quag

[11] Patent Number: 4,746,507

[45] Date of Patent: May 24, 1988

[54] EDHPA BASED CONTRAST AGENTS FOR MR IMAGING, APPARATUS AND METHODS

[75] Inventor: Steven C. Quag, Menlo Park, Calif.

[73] Assignee: Salutar, Inc., Sunnyvale, Calif.

[21] Appl. No.: 719,165

[22] Filed: Apr. 2, 1985

[51] Int. Cl.⁴ ............................................. A61K 49/00
[52] U.S. Cl. ........................................ 424/9; 128/653; 128/654; 514/499; 514/501; 514/510; 514/730; 514/741; 514/748; 514/836; 534/10; 534/15; 534/16; 556/50; 556/61; 556/116; 556/148
[58] Field of Search ............... 532/113, 115, 146, 150; 514/499, 501, 510, 730, 741, 748, 836; 556/116, 148, 61, 50; 424/9; 128/653, 654; 534/15, 16, 10

[56] References Cited

U.S. PATENT DOCUMENTS

| 2,795,550 | 6/1957 | Harle et al. | 556/63 |
| 4,442,305 | 4/1984 | Weitl et al. | 514/836 |
| 4,647,447 | 3/1987 | Gries et al. | 424/2 |

FOREIGN PATENT DOCUMENTS 8633082  1/1983  Australia.

OTHER PUBLICATIONS

Pykett, I. L., Sci. Am., May 1982, pp. 78–88.

*Primary Examiner*—Robert J. Warden
*Assistant Examiner*—Stephen C. Wieder
*Attorney, Agent, or Firm*—Sprung Horn Kramer & Woods

[57] ABSTRACT

Ethylene Diamine Hydroxy Phenylacetic Acid (EDHPA) type chelators strongly bind paramagnetic metal ions to provide excellent contrast agents for magnetic resonance (MR) imaging. The magnetic dipole generated by unpaired electrons within the paramagnetic (PM) atom, causes a local reduction in the bulk magnetic field of the MR system. The resulting shortening of the T1 (spin lattice) relaxation time in the hydrogen protons within the area of interest, causes an intense "free induction signal" and a corresponding modulation in the collected scanning data. The tissue of organ of interest appears on the MR display as a high intensity of white area. Background tissue is displayed as darker or lower intensity greys. Each member chelator EDHPA' of the EDHPA family of chelators, is a phenolic analog of EDTA, with variations in the para position radical (PR) of the phenol ring. Each EDHPA' chelator is formed by twin amino acid molecules (phenylalanine etc), which provide twin chelation units having three coordination points each for binding the paramagnetic metal.

38 Claims, 5 Drawing Sheets

FIG. IA
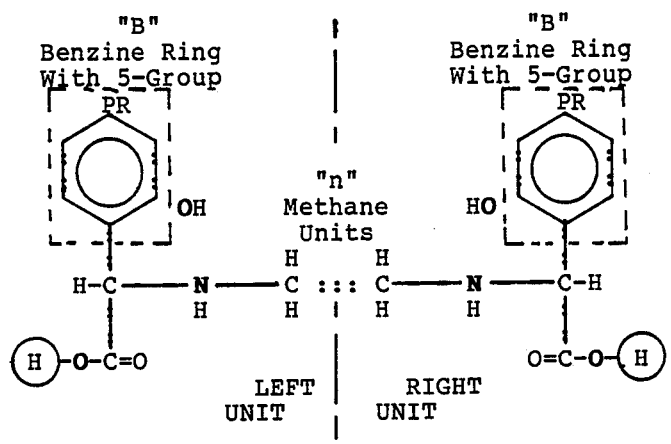
FIG. IB
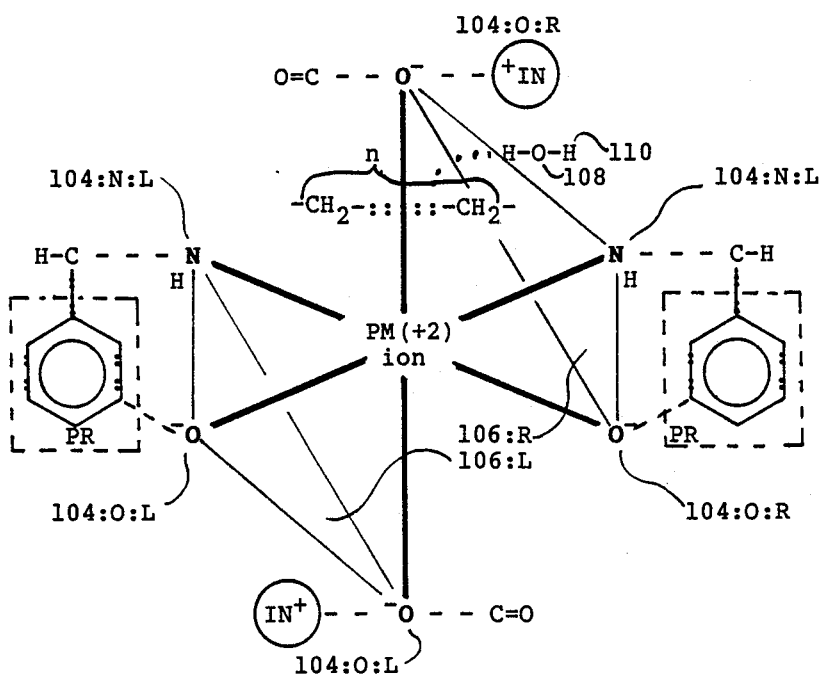

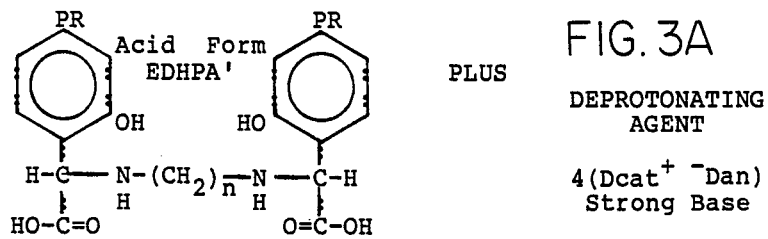
FIG. 3A
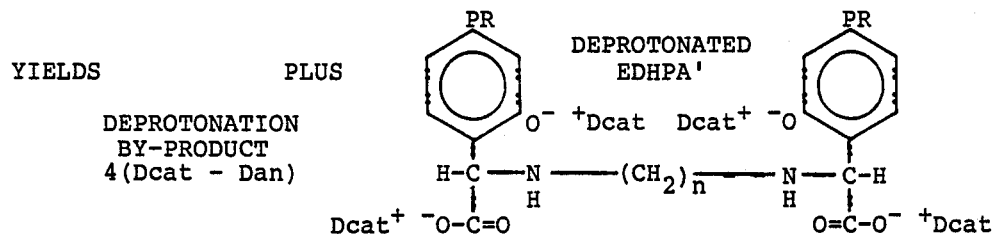
FIG. 3B
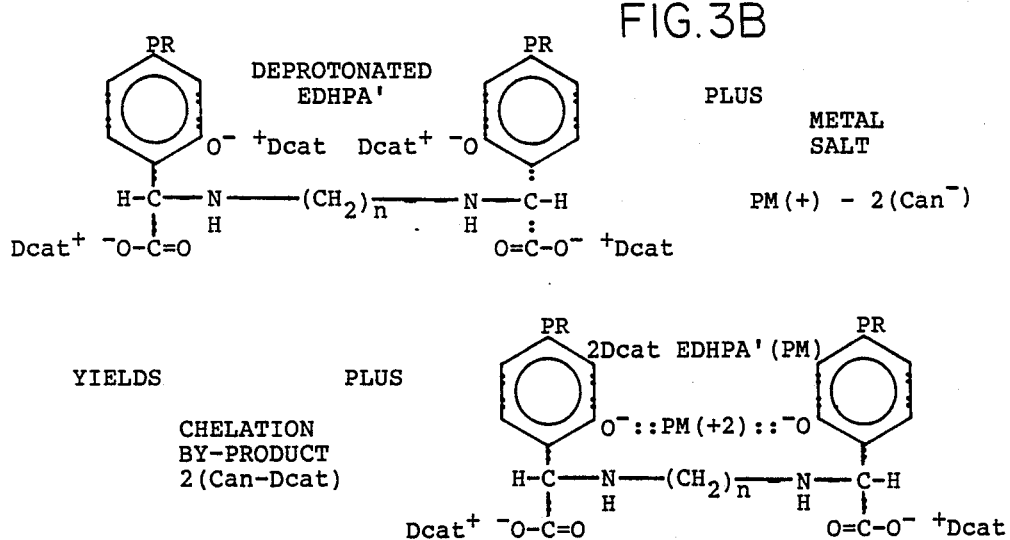
FIG. 3C
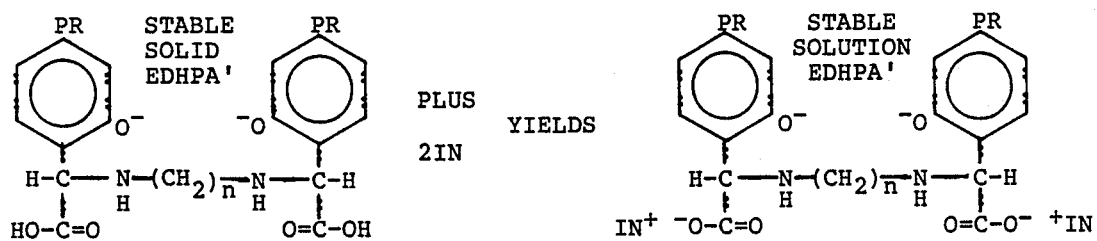

EDHPA BASED CONTRAST AGENTS FOR MR IMAGING, APPARATUS AND METHODS

TECHNICAL FIELD

This invention relates to MR contrast agents, and more particularly to EDHPA (ethylene diamine hydroxy phenylacetic acid) based contrast agents.

BACKGROUND

Schering (No. 3,129,906 Germany) by Gries, Rosenberg, and Weinstien teaches the incorporation of paramagnetic metals into diethylene triamine pentaacetic acid (DTPA) forming chelates useful as contrast agents in magnetic resonance imaging.

Kroll et al (U.S. Pat. No. 3,038,793) teaches the use and manufacture of ethylene diamine diacetic acids containing phenolic groups, of the form N,N'-bis(2-hydroxy-5-Radical benzyl) ethylene diamine diacetic acid.

SUMMARY

It is therefore an object of this invention to provide improved EDHPA based contrast agents for MR imaging, and method of manufacture.

It is another object of this invention to provide MR contrast agents which have a high stability, a low toxicity and are physiologically tolerable.

It is a further object of this invention to provide contrast agents which are in vivo responsive.

It is a further object of this invention to provide contrast agents which are organ selective.

It is a further object of this invention to provide a method of manufacturing such contrast agents.

It is a further object of this invention to provide such a method of manufacturing EDHPA based contrast agents in which the chelation step is faster.

It is a further object of this invention to provide such a method of manufacturing EDHPA based contrast agents which results in a higher yield.

It is a further object of this invention to provide a method of using such contrast agents.

It is a further object of this invention to provide an MR system employing such contrast agents.

Briefly, these and other objects of the present invention are accomplished by providing chemically stable physiologically tolerable EDHPA based contrast agents (and homologs thereof) in a pharmacological state, for in vivo use during diagnostic magnetic resonance (MR) imaging. The contrast agents are either:
of the bivalent form:

$$2(O-\text{``B''}-C_2OO\text{``IN''}-NH)-(CH_2)_n ::: (\text{``PM''}+2),$$

or of the tri-valent form:

$$2(O-\text{``B''}-C_2OO\text{``2IN''}-NH)-(CH_2)_n ::: (\text{``PM''}+3).$$

"PM" is either a bi-valent or tri-valent paramagnetic metal ion. "B" is a benzene ring with an ortho position Oxygen alone, or with an ortho position Oxygen plus a para position phenol radical selected from the group of radicals consisting of alkyl, carboxyl, nitro, and sulfonic acid. The "n" subscript is the number of methyl groups within the $CH_2$ chain connecting the two Nitrogens. "IN" is an inert cation selected from the group of cations consisting of Methyl Glucamine, N-Methyl Glucamine, and a first column mineral salt cation, for balancing the charge on the contrast agent molecule. The contrast agent may be in the stable solid state of EDHPA(PM) IN, or in the stable solution state of EDHPA(PM) anions and IN cations. The method of manufacture includes a deprotonation step in which a strong base is employed to pull the Hydrogen protons away from the EDHPA base material (acid form). The resulting EDHPA(−4) ion chelates rapidly with the paramagnetic metal ions into the bi-valent or tri-valent ionic forms EDHPA(PM)(−2) or EDHPA(PM)(−1). The paramagnetic metal ion PM reduces the T1 relaxation time of local protons within the subject.

BRIEF DESCRIPTION OF THE DRAWING

Further objects and advantages of the present paramagnetic contrast agents, and the method of manufacture and use thereof, will become apparent from the following detailed description and drawing in which:

FIG. 1A is a diagram showing the general chemical structure of the EDHPA family of chelators used in the manufacture of the present EDHPA(PM) contrast agents;

FIG. 1B is a diagram showing the general chelate structure (and water of hydration) of the present EDHPA(PM) contrast agents in bivalent form;

FIGS. 3A-C are diagrams showing the Deprotonation Step, the Chelation Step, and the Solution Formation Step of the method of making the present contrast agents;

EDHPA FAMILY OF CONTRAST AGENTS (FIGS. 1A–1B)

Figure 2A:
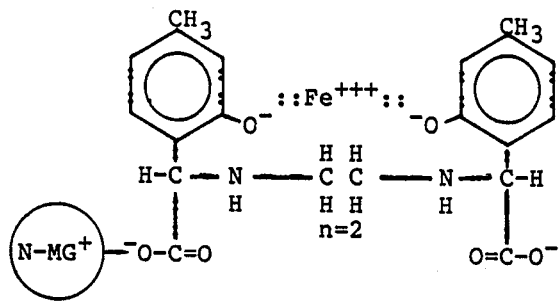
FIGS. 2A-D are diagrams showing the specific chemical structure of various EDHPA'(PM) contrast agents.
Figure 2B:
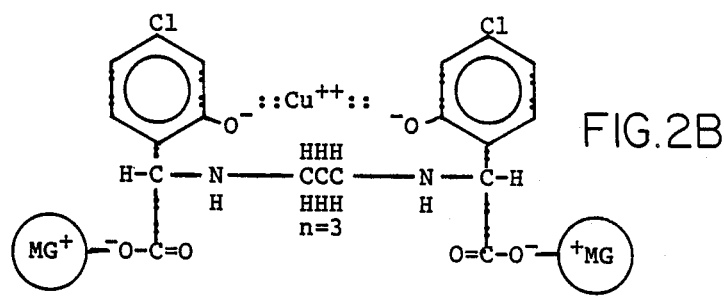
Figure 2C:
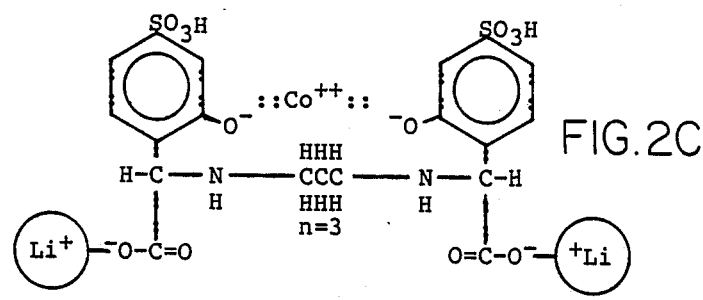
Figure 2D:
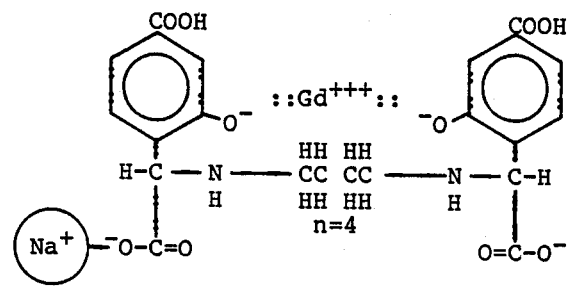

The present paramagnetic contrast agents are formed by Ethylene Diamine Hydroxy Phenylacetic Acid (EDHPA) and derivatives thereof, defining a family of EDHPA based chelators (EDHPA'). The EDHPA based chelators are phenolic analogs of the chelator Ethylene Diamine Tetraacetic Acid (EDTA); and are of the general form below (shown in more detail in FIG. 1A):

$$\begin{array}{ccc}
\text{B--OH} & & \text{HO--B} \\
| & & | \\
\text{H--C--N--}(CH_2)_x\text{--N--C--H} \\
| \quad | & & | \quad | \\
\text{H} & & \text{H} \\
| & & | \\
\text{HO--C=O} & & \text{O=C--OH}
\end{array}$$

where:

"B" is a benzene ring bonded to the acetic carbon with only the ortho —OH phenol radical shown above, or, with the ortho —OH phenol radical plus a para position phenol radical selected from the para-radical (PR) group consisting of:

| | |
|---|---|
| alkyl: | $-(CH_2)_n-CH_3$, |
| carboxyl: | $-COOH$, |
| nitro: | $-NO_2$, and |
| sulfonic acid: | $-SO_3H$; | and

"n" is the number of methyl groups in the "methyl backbone" connecting the twin halves of the EDHPA' molecule, and may any whole integer from 2 to 4, inclusive.

The actual contrast agent is formed from the desired EDHPA' chelator by permiting chelation with the desired paramagnetic metal PM, and ionization of (or both) of the acetic groups by formation of salts with inert cations IN+. Each EDHPA' chelator of the EDHPA based family strongly attaches to the paramagnetic metal ion to form an MR contrast agent.

One or more inert cations (IN+) are required to balance the charge on the contrast agent molecule. IN+ may be the chemically inert cation of a simple first column mineral salt such as Na+, Li+, etc.; or a free base organic ion such as Methyl Glucamine (MG) or N-Methyl Glucamine (N-MG).

FIG. 1B shows the probable physical chelation structure of an EDHPA(PM) type contrast agent in bi-valent form:

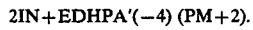

2IN+EDHPA'(−4) (PM+2).

The contrast agent has six polar bonded coordination points 104 (two nitrogen points 104:N and four oxygen points 104:O) which enclose the paramagnetic ion PM+2 on all sides forming a hexadentate structure.

The six bold solid lines shown in FIG. 1B extending from the PM+2 ion represent chelation bonding between the six coordination points and the paramagnetic metal ion.

The two triangles 106:L and 106:R in light solid lines represent the twin left and right, three point chelation units, which are positioned in opposed relationship around the paramagnetic metal. The left unit 106:L is formed by one Nitrogen (104:N:L), one ortho Oxygen (104:O:L), and one COO Oxygen (104:O:L). The right unit 106:R is similarly formed by one Nitrogen (104:N:R), one ortho Oxygen (104:O:R), and one COO Oxygen (104:O:R). The stability (association constant) of each chelator EDHPA' within the EDHPA family, is primarily a function of:

(1) the size of the twin triangles 106, that is the distance between the Nitrogen and two Oxygens forming each triangle;
and
(2) the space between the twin triangles, which is determined by the number of methyl units in the methyl backbone extending between the two Nitrogens.

The second factor may be varied by selecting a particular homolog of the EDHPA' chelator.

The dashed lines shown in FIG. 1B represent chemical bonding within the chelator EDHPA'. These chemical bonds are shown in traditional form in FIG. 1A.

CHARGE BALANCE OF CONTRAST AGENTS

Two inert IN+ ions are required to balance the minus four charge on the EDHPA molecule as follows:

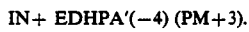

| IN | IN | EDHPA | (PM +2) | |
|---|---|---|---|---|
| +1 | +1 | −4 | +2 | = 0 |

The four oxygen minus charges at points 104:O are balanced by the two positive charges from the (PM+2) ion combined with the two posiive charges from added inert cations "IN+". These bivalent contrast agents have three ion particles in solution for each chelated metal atom, yielding a particle to PM ratio to 3:1. The particle (osmolarity) to paramagnetic (molar relaxivity) ratio for bivalent contrast agents is 3:1.

Contrast agents with trivalent paramagnetic metals are of the general form:

IN+ EDHPA'(−4) (PM+3).

The trivalent form requires only one inert IN+ ion to balance the minus four charge on the contrast agent molecule as follows:

| | EDHPA(PM +2) Charge Balance | | |
|---|---|---|---|
| IN | EDHPA | (PM +3) | |
| +1 | −4 | +3 | = 0 |

These trivalent contrast agents have two ion particles in solution for each chelated metal atom. The particle (osmolarity) to paramagnetic (molar relaxivity) ratio for trivalent contrast agents is 2:1.

PARAMAGNETIC EFFECT EDHPA'(PM)

The above EDHPA'(PM+2) and EDHPA'(PM+3) contrast agents have a paramagnetic effect similar to the Schering EDTA-(PM) contrast agent. For example, IN-EDHPA(Gd+3) requires a concentration of about 3.31 mM to produce a T1 relaxation time of 67 msec (10 MHz field strength, using an RADX). The concentration of Schering DTPA(Gd+3) required to produce a similar result is about 3.16.

Possibly the water of hydration 108 (see FIG. 1B) which collects around the CH2 groups offers a reliable source of protons (H+) 110 for resonanting with the applied MR fields. Protons 110 have a high probability of being present within the local magnetic field of the PM ions. These protons form a class of protons for MR imaging which is distinct from random in vivo protons. The prolonged association time of bound water 108, and the close proximity of protons 110 to the PM ion, establishes a definite and distinct T1 relaxation time which is longer than the T1 for random protons. As a result, protons 110 provided by the water of hydration appear at a higher intensity in the MR image.

EDHPA' HOMOLOGS (FIGS. 3A-D)

Each EDHPA' chelator of the EDHPA family of contrast agents includes the following three methyl homologs:

(1) Ethylene Diamine 0-Hydroxy "PR" Phenylacetic Acid
(EDHPA) having n=2,
(2) Propylene Diamine 0-Hydroxy "PR" Phenylacetic Acid
(PDHPA) having n=3, and (3) Butylene Diamine 0-Hydroxy "PR" Phenylacetic Acid (BDHPA) having n=4.

The methyl backbone dimension between the twin portions of the chelator molecule may be selected from two, three, or four methyl groups, in order to accommodate different sizes of the paramagnetic metal ions.

The stability of the resulting contrast agent increases dramatically by matching the size of the EDHPA' chelator backbone to the ionic radius of the selected paramagnetic metal ion. The ionic radii of the paramagnetic metal ions range as listed below:

| | |
|---|---|
| $Co + 3$ | 0.63 Angstrom units, |
| $Fe + 3$ | 0.64 Angstrom units, |
| $Co + 2$ | 0.72 Angstrom units, |
| $Cu + 3$ | 0.72 Angstrom units, |
| $Fe + 2$ | 0.74 Angstrom units, |
| $Mn + 2$ | 0.80 Angstrom units, |
| $Gd + 3$ | 0.939 Angstrom units, |

In general, adding a single methylene group increases the chelator dimension by about 0.22 Angstrom units. The corresponding increase in PM diameter accommodation is somewhat less due to bending in the $CH_2$ chain.

Three methyl groups appears to provide contrast agents with highest stability for most of the PM ions.

A typical n=2 homolog is N-MG EDHMPA(Fe+3) (Ethylene Diamine Hydroxy Methyl Phenylacetic Acid) shown in FIG. 3A; having the chemical name: ethylenediamine-N,N'-bis(2-hydroxy-5-methylphenyl glycine).

Another typical n=2 homolog is MG-EDHClPA(-Cu+2) (Ethylene Diamine Hydroxy Chlorine Phenylacetic Acid) shown in FIG. 3B; having the chemical name: ethylenediamine-N,N'-bis(2-hydroxy-5-chlorine phenyl glycine).

A typical n=3 homolog is Li-PDHSPA-(Co+2) (Propylene Diamine Hydroxy Sulfo Phenylacetic Acid) shown in FIG. 3C; having the chemical name: propelenediamine-N,N'-bis(2-hydroxy-5-sulfophenyl glycine).

A typical n=4 homolog is Na-BDHCPA-(Gd+3) (Butylene Diamine Hydroxy Carboxy Phenylacetic Acid shown in FIG. 3D; having the chemical name: butylenediamine-N,N'-bis(2-hydroxy-carboxyphenyl glycine).

ORGAN SELECTIVE

Venously introduced contrast agents are instantly distributed throughout the circulatory system for imaging. The vital organs in immediate association with the circulatory system receive substantial blood flow; and provide selective images which are agent enhanced.

Images of the liver and hepatobiliary organs may be obtained by using halide and alkyl para radicals. Contrast agents with these phenol radicals bind with serum lipo-proteins, and are processed through the liver for imaging.

Images of the urinary track may be obtained by using sulfonic and carboxl para radicals. Contrast agents with these phenol radicals are charged and do not bind with serum lipo-proteins, and are therefore rapidly eliminated by the kidneys.

The Nitro group radicals are polar (not charged), and may be employed in both the urinary and hepatobiliary systems.

METHOD OF MANUFACTURE (FIGS. 3A 3B 3C)

A general deprotonation method for making the contrast agents involves treating a select EDHPA' base chelator with a selected paramagnetic metal PM, to provide a EDHPA'-(PM) contrast agent having the desired paramagnetic and chemical properties.

STEP (1) PROVIDING INITIAL SOLVENT for the deprotonation (Step 3) and chelation (Step 4) reactions. The initial solvent should be a suitable volatile liquid, preferably an alcohol such as methanol.

STEP (2) PROVIDING EDHPA' in the powder acid form in the initial solvent by dissolving a suitable EDHPA' compound.

(STEP 3) DEPROTONATING the four oxygen coordinate sites 104:O on the EDHPA' molecule by adding a suitable deprotonating agent (strong base).

| GENERAL DEPROTONATION STEP (see FIG. 3A) | | |
|---|---|---|
| Acid Form EDHPA' $EDHPA'(-4) - (H^+)_4$ | Plus | Deprotonating Agent $4(Dcat^+ Dan^-)$ (strong base) |
| Yields | | |
| Deprotonated EDHPA' $EDHPA'(-4) + 4Dcat^+$ (EDHPA'salt) | Plus | Deprotonation By-Product 4(H-Dan) | where:

$Dan^-$ is the deprotonating anion for pulling the protons away from the EDHPA' molecule; and $Dcat^+$ is the deprotonating cation which now occupies the four negatively charged coordination points 104:O.

The deprotonating agent Dcat-Dan may be a suitable strong salt such as NaOH, $NH_4OH$, LiOH, KOH, or CaOH. Ammonium hydroxide is preferred, because it goes off as $NH_3$ gas and water during the heating of Step 7.

(STEP 4) CHELATING to form EDHPA'(PM) by adding the paramagnetic metal ion PM in the form of a suitable compound such as a metal salt.

| GENERAL CHELATION STEP (see FIG. 3b) | | |
|---|---|---|
| Deprotonated EDHPA' $EDHPA'(-4) + 4Dcat^+$ (EDHPA' salt) | Plus | Metal Salt $PM + 2 - 2(Can^-)$ |
| Yields | | |
| Chelated EDHPA' $EDHPA'(PM)^{--} + 2Dcat^+$ | Plus | Chelation By-Product 2(Can-Dcat) | where:

$PM+2$ (the chelation cation) is the paramagnetic metal cation within the added metal salt; and $Can^-$ (the chelation anion) is the counter anion from the added metal salt.

The metal salt may be any suitable salt with good ionization properties such as metal halides.

For purposes of illustration, a bivalent paramagnetic metal is shown with a simple monovalent salt anion. However, other valence configurations may be employed.

(Step 5) AGITATE the solution to complete the chelation process.

(Step 6) PROVIDE $IN^+$ ions in the solution. The $IN^+$ may be a mineral ion such as $Li^+$, $Na^+$ etc from a corresponding mineral salt such as mineral hydroxide. The OH⁻ anion of the mineral hydroxide forms water and is removed in STEP 7. Alternatively, the IN+ may be an inert free base ion such as Methyl Glucamine (MG+) or N-Methyl Glucamine (N-MG+).

(Step 7) FORM STABLE EDHPA'(PM) SOLID by removing the initial solvent, the unused deprotonating agent (Dcat+-Dan−), the remaining by-products (H-Dan and Can-Dcat), and the two Dcat+ ions from the two O=C—O− coordination points on each EDHPA'(PM) molecule. This removal is preferably accomplished by heating the solution under a partial vacuum. The solvent, agents and products are selected to be volatile, or to degrade thermally at this stage and go off as a gas. The residue remaining is a stable solid form of the two compounds EDHPA'(PM) and IN, which has an indefinite shelf life, and may be readily stored and shipped.

(Step 8) WASH the solution with additional solvent, and heat as in Step 7.

(Step 9) FORM STABLE EDHPA'(PM) SOLUTION by dissolving the the solid form of Step 8 in a suitable solvent such as water, yielding a stable pharmacological solution:

EDHPA (PM)⁻⁻ 2IN+ as shown in FIG. 3C.

(Step 10) FILTER the EDHPA'(PM) solution to remove insolubles.

The deprotonation step assures that the desired chelation binding will occur during the chelation step. Deprotonated EDHPA' is highly soluble, and accelerates the chelation step to an almost instantaneous reaction. The yields of EDHPA'(PM) contrast agents are high (90%+). Chemically active metal ions such as Mn will react with non-deprotonated EDHPA' chelator forming unwanted by-products.

EXAMPLE: EDHPA-(Mn+2) 2(N-MG'+') EMBODIMENT

The following steps may be employed to form the Manganese EDHPA contrast agent:

EDHPA (Mn+2) 2(N-MG+)

using a methanol initial solvent.

(Step 1) FORM N-MG SOLUTION (two molar equivalent) by dissolving 0.6 grams of N-MG (the source of IN+ ions) into 10 ml of anhydrous methanol (the initial solvent). Solution formation may be accelerated by heating the initial methanol solvent to about 60 degrees C. The heat may be terminated when the solution becomes clear. Alternatively, the N—MG may be added during the heating step as the solvents and by-products are being removed.

(Step 2) ADD 0.49 grams of EDHPA (Fluka Corp., New York, N.Y.) to the methanol, forming a yellow-orange suspension.

(Step 3) DEPROTONATE the EDHPA with about 2 ml of concentrated NH₄OH (the deprotonating agent):

| EDHPA(−4)(H+)₄ | Plus | 4(NH₄+ OH−) |
|---|---|---|
| Yields | | |

| EDHPA(−4) + 4NH₄+ | Plus | 4H₂O |
|---|---|---| forming a golden-brown solution.

(Step 4) CHELATE (Mn+2) by adding MnCl₂ to the golden-brown EDHPA solution in a 1:1 ratio with the EDHPA, using about 0.39 grams of MnCl₂ (with four waters of hydration) in one ml of a suitable volatile solvent such as methanol. Swirl the resulting white MnOH₂ precipitate to dissolve into solution. The Mn+2 chelates within minutes with the EDHPA forming a golden-brown to black solution.

(Step 5) STIR the solution.

(Step 6) PROVIDE N-MG if not included in Step 1.

(Step 7) FORM STABLE EDHPA-(Mn+2) POWDER by rotary evaporation. The NH₄+ and OH− ions thermally decompose into NH₃ gas and water; and the methanol and water evaporate forming a dry, stable powder.

(Step 8) WASH the solution with methanol.

(Step 9) FORM STABLE EDHPA-(Mn+2) SOLUTION by adding water (48 mM, pH of about 6.5).

(Step 10) FILTER the solution with a Whatman type number 1 filter.

STABLE-SOLID STATE

EDHPA-(PM) contrast agents have an indefinite shelf life in the stable solid state of Step 8. The contrast agents may be shipped and stored in the stable solid state.

Alternatively, contrast agents in the stable solution state of Step 9 (water or other solvent); may be packaged in storage vials, and frozen under a vacuum. The low pressure sublimates the solvent, leaving crystals of the contrast agent. The vial is sealed to prevent entry of external contaminants, and to preserve the internal vacuum. The resulting freeze-dried, vacuum sealed powder, is highly stable and free from environmental degradation effects. An individual injection may be contained in each storage vial.

STABLE PHARMACOLOGICAL-SOLUTION STATE

Prior to injection, the stable solid contrast agent may be raised to the pharmacological state by the addition of a suitable solvent such as water, serum, albumin solutions, or saline. A typical injection contains about 1–2 grams of EDHPA(PM) material in 10–50 mL.

The storage vial may have twin compartments containing the desired amounts of powdered EDHPA-(PM) and solvent for a single application. When the seal between the compartments is broken, the EDHPA-(PM) goes into solution at the desired concentration for immediate use. The EDHPA-(PM) solution mixes readily with the in vivo fluids.

PARAMAGNETIC EXAMPLES

The paramagnetic material PM may be any paramagnetic metal ion, including the following metal ions:

| IONS OF TRANSITION ELEMENTS | | | |
|---|---|---|---|
| Cr + 3 | 24 (Chromium) | Co + 2 | 27 (Cobalt) |
| Mn + 2 | 25 (Manganese) | Ni + 2 | 28 (Nickel) |
| Fe + 3 | 26 (Iron) | Cu + 3 | 29 (Copper) |
| Fe + 2 | 26 (Iron) | Cu + 2 | 29 (Copper) |

| IONS OF LANTHANIDE ELEMENTS | | | |
|---|---|---|---|
| La + 3 | 57 (Lanthanum) | Gd + 3 | 64 (Gadolinium) |
| Ce + 3 | 58 (Cerium) | Tb + 3 | 65 (Terbium) |
| Pr + 3 | 59 (Praseodymium) | Dy + 3 | 66 (Dysprosium) |
| Nd + 3 | 60 (Neodymium) | Ho + 3 | 67 (Holmium) |
| Pm + 3 | 61 (Promethium) | Er + 3 | 68 (Erbium) |
| Sm + 3 | 62 (Samarium) | Tm + 3 | 69 (Thulium) |
| Eu + 3 | 63 (Europium) | Yb + 3 | 70 (Ytterbium) |
|  |  | Lu + 3 | 71 (Lutetium) |

Gd has the highest paramagnetic property; but is a costly and highly toxic in the free state. Placing the Gd within the chelator produces a physiologically tolerable form of Gd; but also reduces paramagnetic effect of the Gd. The chelate structure tends to shield the paramagnetic ions and prevents close proximity to local $H^+$ water protons. Fe and Mn have a high paramagnetic property and excellent physiological tolerance. Both of these paramagnetic ions are normally present in the physiological environment.

Figure 4:
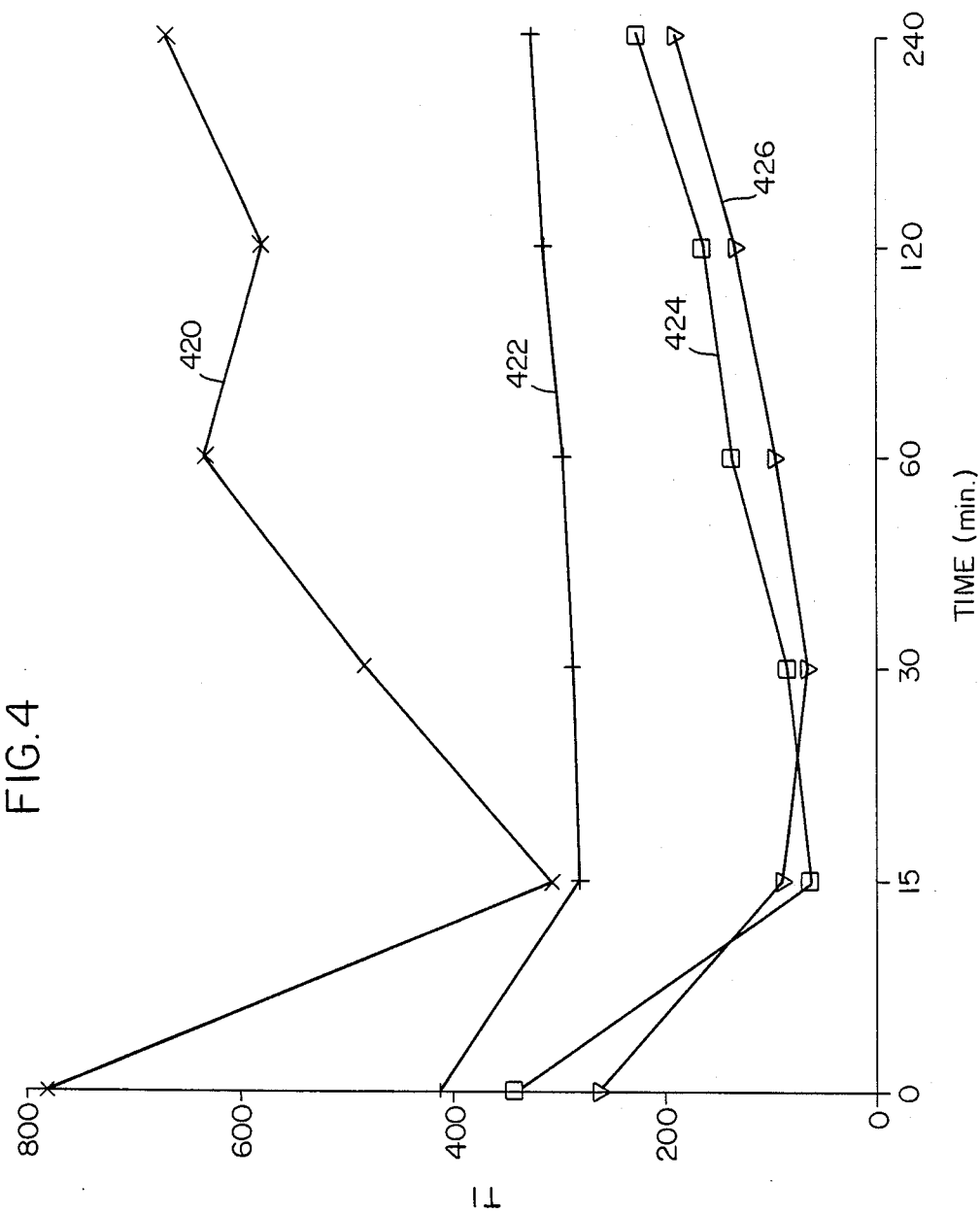
FIG. 4A is a flow chart showing a method of using the EDHPA'(PM) paramagnetic contrast agents.
FIG. 4B is a plot of T1 verses post injection time for EDHPA(Mn) showing the optimum MR image window for various organs.
Figure 5:
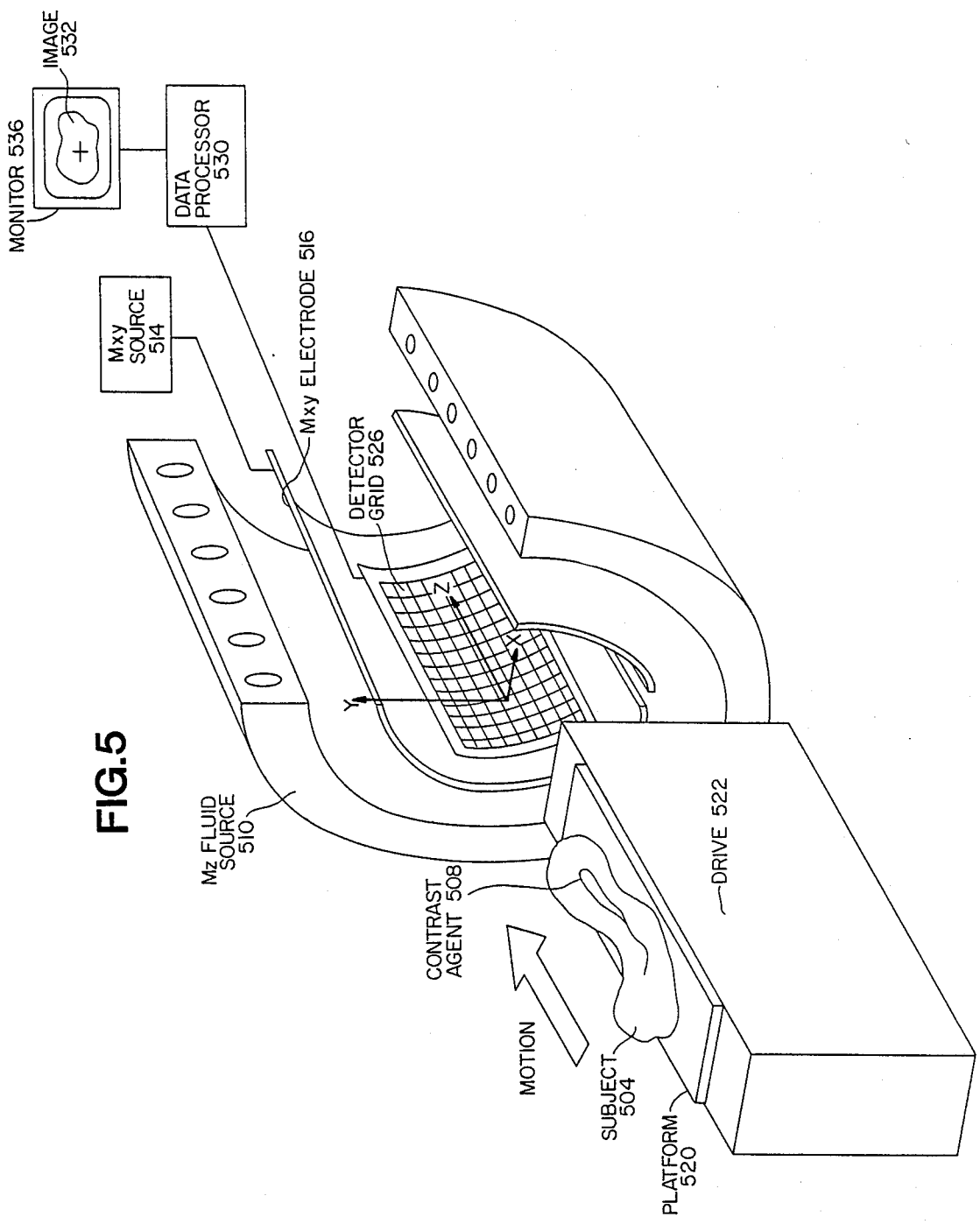
FIG. 5 is a cut-away perspective view of an MR system showing the motion platform and subject using EDHPA(PM) paramagnetic contrast agents.

METHOD OF USE (FIGS. 4A and 4B)

FIG. 4A shows T1 (spin lattice) relaxation time plotted against post injection time for skeletal muscle (curve 420), renal cortex (curve 422), renal medella (curve 424) and the liver (curve 426). In each case, an optimum imaging window appears at about 15–30 minutes after injection.

FIG. 4B shows a method of imaging subject 504 with MR system 500 employing paramagnetic contrast agent 508.

(Step 1) PROVIDING a physiologically tolerable contrast agent 508 in the form:

IN-EDHPA′(PM+2) or IN-EDHPA′(PM+2).

If initially in powder form, the IN-EDHPA(PM) contrast agent must be dispensed into a suitable carrier vehicle.

(Step 2) INTRODUCING the IN-EDHPA(PM) contrast agent into subject 508 (preferably by intravenous injection).

(Step 3) WAITING for about 15 to 30 minutes for the contrast agent to distribute within the in vivo environment.

(Step 4) IMAGING the subject with MR system 500 to obtain an enhanced MR image.

Comparison or subtraction imaging, requires an initial step of providing data from a prior MR imaging, and the final step of subtraction comparing the prior MR image with the current MR image. A historical base line image from the subjects file may be employed as the prior image. Alternatively, a current MR image made without the use of a contrast agent may be employed.

GENERAL MR SYSTEM (FIG. 5)

Magnetic resonance (MR) imaging system 500 has two magnetic components which scan subject 504 for obtaining MR data enhanced by the presence of contrast agent 508. Bulk magnetic field Mz from Z field source 510 causes paramagnetic particles such as local hydrogen protons within the subject to aline with the Z axis. Periodic or rotating field Mxy from XY field generator 514 extends between XY electrodes 516. The subject to be scanned is positioned on support platform 520 and moved through the magnetic fields by drive 522. Rotating field Mxy is tuned to cause resonant precession of the local protons within the tissue of interest. Each local proton precesses about the Z axis in response to a particular frequency of rotating field Mxy. When rotating field Mxy is removed, the precessing protons decay back into alinement with Mz.

The decay period of the local protons (spin lattice relaxation time T1) varies between organs and between conditions within the same organ. Tumor tissue tends to have a longer T1 than healthy tissue. The presence of the paramagnetic metal ions PM causes a shortening of the proton T1, without substantially affecting T2 (spin-spin relaxation time). The energy of precession is released forming a free induction signal. Grid detector 526 senses the decay signals which are stored and processed by data processer system 530. to form an image 532 on monitor 536. The metal ion in the contrast agent are not directly imaged by the MR system.

The imaging system is further disclosed in Scientific American, May 1982, pages 78–88, and "NMR A Primer for Medical Imaging" by Wolf and Popp Slack Book Division (ISBN 0-943432-19-7), which disclosures are hereby incorporated by reference.

INDUSTRIAL APPLICABILITY

It will be apparent to those skilled in the art that the objects of this invention have been achieved as described hereinbefore by providing an improved physiologically tolerable contrast agents and method of manufacture. The contrast agent has a high association constant due to the homolog selection. The variability of the para benzene structure permits a range of vivo response and organ selection.

CONCLUSION

Clearly various changes may be made in the structure and embodiments shown herein without departing from the concept of the invention. Further, the features of the embodiments shown in the various Figures may be employed with the embodiments of the other Figures.

Therefore, the scope of the invention is to be determined by the terminology of the following claims and the legal equivalents thereof.

I claim as my invention:

1. An EDHPA based contrast agent in a solid state form, for use in an in vivo solution during diagnostic magnetic resonance (MR) imaging, to enhance the MR image of the region of interest of a subject within the magnetic field of the MR system, having the general formula:

$$\begin{array}{c} B-O^- \quad (PM + 2) \quad ^-O-B \\ | \qquad\qquad\qquad\qquad\qquad\qquad | \\ H-C-N-(CH_2)_n-N-C-H \\ | \quad\; H \qquad\qquad\qquad H \quad\; | \\ IN^{+\,-}O-C=O \qquad\qquad\qquad O=C-O^{-\,+}IN \end{array}$$

or $$\begin{array}{c} B-O^- \quad (PM + 3) \quad -O-B \\ | \qquad\qquad\qquad\qquad\qquad\qquad | \\ H-C-N-(CH_2)_n-N-C-H \\ | \quad\; H \qquad\qquad\qquad H \quad\; | \\ IN^{+\,-}O-C=O \qquad\qquad\qquad O=C-O^- \end{array}$$

where:

"PM" is a paramagnetic metal ion bound by chelation within the EDHPA;

"B" is a benzene ring bonded to the acetic carbon, with only the "$O^-$" phenol radical at the ortho position, or, a benzene ring bonded to the acetic carbon, with the "O⁻" phenol radical plus a para position phenol radical selected from the group consisting of

| alkyl: | —(CH₂)—CH₃, |
|---|---|
| carboxyl: | —COO⁻, |
| nitro: | —NO₂, and |
| sulfonic acid: | —SO₃⁻; |

"n" is, from 2 to 4 inclusive, methyl groups within the methyl chain connecting the two Nitrogen atoms; and "IN⁺" is a chemically inert cation for balancing the charge of the contrast agent molecule;

whereby the contrast agent causes a reduction in the T1 relaxation timer near the region of interest within the subject.

2. The family of contrast agents of claim 1, wherein "IN⁺" is at least one inert cation selected from the group consisting of:
Methyl Glucamine,
N-Methyl Glucamine, and
a first periodic group mineral salt cation.

3. The family of contrast agents of claim 1, wherein "n" is the whole integer 3.

4. The contrast agent of claim 1, wherein the paramagnetic metal ion "PM" is an ion selected from the group consisting of:

| Cr + 3 | Co + 2 |
|---|---|
| Mn + 2 | Ni + 2 |
| Fe + 3 | |
| Fe + 2 | Cu + 2 |
| La + 3 | Gd + 3 |
| Ce + 3 | Tb + 3 |
| Pr + 3 | Dy + 3 |
| Nd + 3 | Ho + 3 |
| Pm + 3 | Er + 3 |
| Sm + 3 | Tm + 3 |
| Eu + 3 | Yb + 3 and |
| | Lu + 3. |

5. THe contrast agent of claim 1, wherein the paramagnetic metal ion "PM" is an ion selected from the group consisting of:

| Cr + 3 | Co + 2 |
|---|---|
| Mn + 2 | Ni + 2 |
| Fe + 3 | |
| Fe + 2 | Cu + 2 and |
| Gd + 3. | |

6. The contrast agent of claim 1, wherein the paramagnetic metal ion "PM" is an ion selected from the group consisting of:

| Fe + 3 | Co + 2 |
|---|---|
| Mn + 2 | Cu + 2 and |
| Gd + 3. | |

7. An EDHPA based contrast agent in a pharmacological solution form, for use in vivo solution during diagnostic magnetic resonance (MR) imaging, to enhance the MR image of the region of interest of a subject within the magnetic field of the MR system, having the general formula:

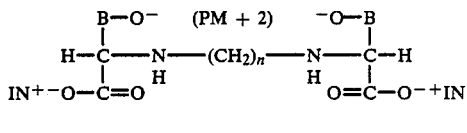

or

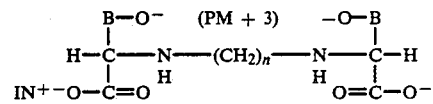

where:
"PM" is a paramagnetic metal ion bound by chelation within the EDHPA;

"B" is a benzene ring bonded to the acetic carbon, with only the "O⁻" phenol radical at the ortho position, or, a benzine ring bonded to the acetic carbon, with the "O⁻" phenol radical plus a para position phenol radical selected from the group consisting of

| alkyl: | —(CH₂)—CH₃, |
|---|---|
| carboxyl: | —COO⁻, |
| nitro: | —NO₂, and |
| sulfonic acid: | —SO₃⁻; |

"n" is, from 2 to 4 inclusive, methyl groups within the methyl chain connecting the two Nitrogen atoms; and "IN⁺" is a chemically inert cation for balancing the charge the contrast agent molecule;

and a pharmaceutically acceptable vehicle means for dispersing the EDHPA(PM) contrast agent; whereby the contrast agent causes a reduction in the T1 relaxation time near the region of interest within the subject.

8. The contrast agent of claim 7, wherein the vehicle means is a water solution.

9. The family of contrast agents of claim 7, wherein "IN⁺" is at least one inert cation selected from the group consisting of
Methyl Glucamine,
N-Methyl Glucamine, and
a first periodic group mineral salt cation.

10. The family of contrast agents of claim 7, wherein "n" is the whole integer 3.

11. The contrast agent of claim 7, wherein the paramagnetic metal ion "PM" is an ion selected from the group consisting of:

| Cr + 3 | Co + 2 |
|---|---|
| Mn + 2 | Ni + 2 |
| Fe + 3 | |
| Fe + 2 | Cu + 2 |
| La + 3 | Gd + 3 |
| Ce + 3 | Tb + 3 |
| Pr + 3 | Dy + 3 |
| Nd + 3 | Ho + 3 |
| Pm + 3 | Er + 3 |
| Sm + 3 | Tm + 3 |
| Eu + 3 | Yb + 3 and |
| | Lu + 3. |

12. The contrast agent of claim 7, wherein the paramagnetic metal ion "PM" is an ion selected from the group consisting of:

| | |
|---|---|
| Cr + 3 | Co + 2 |
| Mn + 2 | Ni + 2 |
| Fe + 3 | |
| Fe + 2 | Cu + 2 and |
| Gd + 3. | |

13. The contrast agent of claim 7, wherein the paramagnetic metal ion "PM" is an ion selected from the group consisting of:

| | |
|---|---|
| Fe + 3 | Co + 2 |
| Mn + 2 | Cu + 2 and |
| Gd + 3. | |

14. A method of manufacture of a chemically stable physiologically tolerable contrast agent EDHPA'(PM) by deprotonating and chelating the corresponding EDHPA based chelator, for use in vivo solution during diagnostic magnetic resonance (MR) imaging, to enhance the MR image of the region of interest of a subject within the magnetic field of the MR system, comprising:

PROVIDING INITIAL SOLVENT for the deprotonating and chelating steps;

PROVIDING to the solvent EDHPA based chelator having the general form:

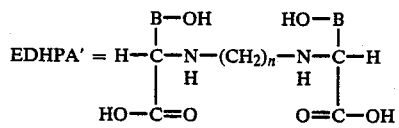

where:
"B" is a benzene ring bonded to the acetic carbon,
- with only the "OH" phenol radical at the ortho position,
or, a benzene ring bonded to the acetic carbon, bonded with the "OH" phenol radical plus a para position phenol radical selected from the group consisting of

| | |
|---|---|
| alkyl: | —(CH$_2$)—CH$_3$, |
| carboxyl: | —COOH, |
| nitro: | —NO$_2$, and |
| sulfonic acid: | —SO$_3$H; | and
"n" is, from 2 to 4 inclusive, methyl groups within the methyl chain connecting the two Nitrogen atoms;

DEPROTONATING THE EDHPA' by adding a strong base deprotonating agent for removing the protons from the four oxygen coordinate sites:

| EDHPA Based Chelator | Plus | Deprotonating Agent |
|---|---|---|
| EDHPA'(−4) − (H$^+$)$_4$ | | 4(Dcat$^+$ Dan$^-$) |
| Yields | | |
| Deprotonated EDHPA' | Plus | Deprotonation By-Product |
| EDHPA'(−4) + 4Dcat$^+$ | | 4(H-Dan) |
| (EDHPA' salt) | | | where:
Dan$^-$ is a deprotonating anion for pulling the protons away from the EDHPA' chelator, and Dcat$^+$ is a deprotonating cation which occupies the four negatively charged coordination points, to provide the EDHPA'(−4) ion in solution;

CHELATING THE EDHPA'(−) to form EDHPA'(PM) by adding the paramagnetic metal ion in the form of a metal salt:

| Deprotonated EDHPA' | Plus | Metal Salt |
|---|---|---|
| EDHPA'(−4) + 4Dcat$^+$ | | PM + 2 − 2(Can$^-$) |
| Yields | | |
| Chelated EDHPA' | Plus | Chelation By-Product |
| EDHPA'(PM)$^{--}$ + 2Dcat$^+$ | | 2(Can-Dcat) | where:
PM is a paramagnetic metal cation from the added metal salt, and
Can$^-$ is the counter anion from the added metal salt,
to provide the EDHPA based chelator in the contrast agent form of EDHPA'(PM).

15. The method of claim 14, further comprising the additional step of adding an inert cation for balancing the charge on the contrast agent EDHPA'(PM).

16. The method of claim 15, further comprising the additional step of:
FORMING A STABLE EDHPA'(PM) SOLID from the deprotonated chelated EDHPA'(PM) and inert cation by removing:
the initial solvent,
the unused deprotonating agent (Dcat$^+$-Dan$^-$),
the by-products (H-Dan and Can-Dcat), and
the Dcat$^+$ ions from the O=C—O$^-$ coordination points on the EDHPA'(PM).

17. The method of claim 16, wherein the step of forming a stable EDHPA'(PM) solid is accomplished by heating the deprotonated chelated solution.

18. The method of claim 18, wherein the step of forming a stable EDHPA'(PM) solid is accomplished by heating the deprotonated chelated solution under a partial vacuum.

19. The method of claim 18, wherein the step of forming a stable EDHPA'(PM) solid is accomplished by heating the deprotonated chelated solution under a partial vacuum in a rotary evaporator.

20. The method of claim 16, further comprising the additional step of:
FORMING A STABLE EDHPA'(PM) SOLUTION by dissolving the stable solid EDHPA'(PM)-IN in a pharmacologically suitable solvent yielding EDHPA'(PM)$^{--}$ 2IN$^+$, in a stable pharmacological solution.

21. The method of claim 20, wherein the pharmacologically suitable solvent is water.

22. The method of claim 14, wherein the initial solvent provided for the deprotonating and chelating steps is a volatile liquid.

23. The method of claim 22, wherein the initial volatile solvent is an alcohol.

24. The method of claim 23, wherein the initial volatile solvent is methanol.

25. The method of claim 14, wherein the strong base deprotonating agent is at least one member selected from the group consisting of NaOH, NH$_4$OH, LiOH, KOH, and CaOH.

26. The method of claim 14, wherein the strong base deprotonating agent is ammonium hydroxide.

27. The method of claim 1, wherein the Can$^-$ anion in the metal salt is a halide ion.

28. The method of claim 1, wherein Can$^-$ is Cl$^-$.

29. The contrast agent of claim 14, wherein the paramagnetic metal ion "PM" is an ion selected from the group consisting of:

| Cr + 3 | Co + 2 |
|---|---|
| Mn + 2 | Ni + 2 |
| Fe + 3 | |
| Fe + 2 | Cu + 2 |
| La + 3 | Gd + 3 |
| Ce + 3 | Tb + 3 |
| Pr + 3 | Dy + 3 |
| Nd + 3 | Ho + 3 |
| Pm + 3 | Er + 3 |
| Sm + 3 | Tm + 3 |
| Eu + 3 | Yb + 3 and |
| | Lu + 3. |

30. The contrast agent of claim 14, wherein the paramagnetic metal ion "PM" is an ion selected from the group consisting of:

| Cr + 3 | Co + 2 |
|---|---|
| Mn + 2 | Ni + 2 |
| Fe + 3 | |
| Fe + 2 | Cu + 2 and |
| Gd + 3. | |

31. The contrast agent of claim 14, wherein the paramagnetic metal ion "PM" is an ion selected from the group consisting of:

| Fe + 3 | Co + 2 |
|---|---|
| Mn + 2 | Cu + 2 and |
| Gd + 3. | |

32. The method of claim 14, wherein "IN$^+$" is at least one inert cation selected from the group consisting of:
Methyl Glucamine,
N-Methyl Glucamine, and
a first periodic group mineral salt cation.

33. The method of claim 14, further comprising the step of freeze drying the EDHPA'(PM) to form a stable crystal.

34. The method of claim 33, further comprising the step of adding a pharmaceutically acceptable vehicle means for dispersing the EDHPA'(PM) crystal forming the contrast agent.

35. The method of imaging a subject with a magnetic resonance (MR) imaging system employing an EDHPA based paramagnetic contrast agent EDHPA'(PM), comprising the steps of:
PROVIDING a physiologically tolerable contrast agent EDHPA'(PM) having the general form:

$$\begin{array}{c} B-O^- \quad (PM+2) \quad -O-B \\ | \qquad \qquad \qquad \qquad \qquad | \\ H-C-N-(CH_2)_n-N-C-H \\ | \quad\; H \qquad\qquad\quad H \quad | \\ IN^+-O-C=O \qquad\qquad\quad O=C-O^{-+}IN \end{array}$$

or $$\begin{array}{c} B-O^- \quad (PM+3) \quad -O-B \\ | \qquad \qquad \qquad \qquad \qquad | \\ H-C-N-(CH_2)_n-N-C-H \\ | \quad\; H \qquad\qquad\quad H \quad | \\ IN^+-O-C=O \qquad\qquad\quad O=C-O^- \end{array}$$

where:
"PM" is a paramagnetic metal ion bound by chelation within the EDHPA';
"B" is a benzene ring bonded to the acetic carbon, with only the "O$^-$" phenol radical at the ortho position,
or, a benzene ring bonded to the acetic carbon, with the "O$^-$" phenol radical plus a para position phenol radical selected from the group consisting of

| alkyl: | $-(CH_2)-CH_3$, |
|---|---|
| carboxyl: | $-COO^-$, |
| nitro: | $-NO_2$, and |
| sulfonic acid: | $-SO_3^-$; |

"n" is, from 2 to 4 inclusive, methyl groups within the methyl chain connecting the two Nitrogen atoms; and
"IN$^+$" is a chemically inert cation for balancing the charge the contrast agent molecule;
whereby the contrast agent causes a reduction in the T1 relaxation time near the region of interest within the subject;
INTRODUCING the EDHPA'(PM) contrast agent into the subject;
WAITING for the phenol radicals to cooperate with the in vivo environment; and
IMAGING the region of interest within a subject with the MR system to obtain a contrast agent enhanced image.

36. The method of imaging a subject as specified in claim 35, wherein the contrast agent is introduced by intravenous injection.

37. The method of imaging a subject as specified in claim 35, wherein the waiting step last from about fifteen minutes to about thirty minutes.

38. The method of imaging a subject as specified in claim 35, further comprising:
the initial step of providing data from a prior MR imaging: and
the final step of subtraction comparing the prior MR image with the current MR image.

* * * * *

UNITED STATES PATENT AND TRADEMARK OFFICE
CERTIFICATE OF CORRECTION

PATENT NO. : 4,746,507
DATED : May 24, 1988
INVENTOR(S) : Steven C. Quay

It is certified that error appears in the above-identified patent and that said Letters Patent is hereby corrected as shown below:

Title Page, under "United States Patent"  Delete "Quag" and substitute --Quay--

Title Page, "[75] Inventor:"  Delete "Steven C. Quag" and substitute --Steven C. Quay--

Title Page, Abstract, line 11  After "tissue" delete "of" and substitute --or--

Col. 7, line 29  After "EDHPA" insert --'--

Col. 11, line 17  Delete "timer" and substitute --time--

Col. 12, line 20  Delete "benzine" and substitute --benzene--

Col. 14, line 38 and Col. 14, line 42  Delete "claim 18" and substitute --claim 16--

Signed and Sealed this

First Day of November, 1988

*Attest:*

DONALD J. QUIGG

*Attesting Officer*  *Commissioner of Patents and Trademarks*

Notice of Adverse Decision in Interference

In Interference No. 102,404, involving Patent No. 4,746,507, S. C. Quay, EDHPA BASED CONTRAST AGENTS FOR MR IMAGING, APPARATUS AND METHODS, final judgement adverse to the patentee was rendered Dec. 7, 1990, as to claims 1-13 and 35-38.

*(Official Gazette March 5, 1991)*